(12) United States Patent
Liu et al.

(10) Patent No.: US 9,295,397 B2
(45) Date of Patent: Mar. 29, 2016

(54) METHOD AND APPARATUS FOR BEAT-SPACE FREQUENCY DOMAIN PREDICTION OF CARDIOVASCULAR DEATH AFTER ACUTE CORONARY EVENT

(71) Applicant: Massachusetts Institute of Technology, Cambridge, MA (US)

(72) Inventors: Yun Liu, Cambridge, MA (US); John V. Guttag, Lexington, MA (US); Collin M. Stultz, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/305,260

(22) Filed: Jun. 16, 2014

(65) Prior Publication Data

US 2014/0371610 A1 Dec. 18, 2014

Related U.S. Application Data

(60) Provisional application No. 61/835,251, filed on Jun. 14, 2013.

(51) Int. Cl.
*A61B 5/04* (2006.01)
*A61B 5/00* (2006.01)
*A61B 5/08* (2006.01)

(52) U.S. Cl.
CPC ........... *A61B 5/04014* (2013.01); *A61B 5/7267* (2013.01); *A61B 5/7275* (2013.01); *A61B 5/0816* (2013.01)

(58) Field of Classification Search
CPC . A61B 5/7275; A61B 5/04014; A61B 5/0402
See application file for complete search history.

(56) References Cited

U.S. PATENT DOCUMENTS

| | | |
|---|---|---|
| 5,609,158 A | 3/1997 | Chan |
| 5,655,540 A | 8/1997 | Seegobin |
| 5,749,900 A | 5/1998 | Schroeppel et al. |

(Continued)

FOREIGN PATENT DOCUMENTS

| | | |
|---|---|---|
| WO | 94/06350 | 3/1994 |
| WO | 00/10455 | 3/2000 |

OTHER PUBLICATIONS

Tuzcu et al., "Dynamic Time Warping as a Novel Tool in Pattern Recognition of ECG Changes in Heart Rhythm Disturbances," Systems, Man and Cybernetics, 2005 IEEE International Conference on, IEEE, Piscataway, NJ, USA, vol. 1, Oct. 10, 2005, pp. 182-186.

(Continued)

*Primary Examiner* — Robert N Wieland
(74) *Attorney, Agent, or Firm* — K&L Gates LLP (57) ABSTRACT

A method for the machine generation of a model for predicting patient outcome following the occurrence of an event. In one embodiment the method includes the steps of obtaining a physiological signal of interest, the physiological signal having a characteristic; obtaining a time series of a signal characteristic; dividing the time series into a plurality of window segments; converting the time series from time-space to beat-space; computing the power in various frequency bands of each window segment; computing the 90th percentile of the spectral energies across all window segments for each frequency band; and inputting the data into a machine learning program to generate a weighted risk vector.

5 Claims, 5 Drawing Sheets

(56) References Cited

U.S. PATENT DOCUMENTS

| | | |
|---|---|---|
| 5,954,664 A | 9/1999 | Seegobin |
| 6,035,233 A | 3/2000 | Schroeppel et al. |
| 6,223,073 B1 | 4/2001 | Seegobin |
| 6,556,861 B1 | 4/2003 | Prichep |
| 6,571,121 B2 | 5/2003 | Schroeppel et al. |
| 6,571,122 B2 | 5/2003 | Schroeppel et al. |
| 6,748,272 B2 | 6/2004 | Carlson et al. |
| 7,031,765 B2 * | 4/2006 | Ritscher et al. ............ 600/518 |
| 7,069,070 B2 | 6/2006 | Carlson et al. |
| 7,225,013 B2 | 5/2007 | Geva et al. |
| 7,248,919 B2 | 7/2007 | Carlson et al. |
| 7,367,941 B2 | 5/2008 | Silverman et al. |
| 7,539,532 B2 | 5/2009 | Tran |
| 7,599,733 B1 | 10/2009 | Wirasinghe et al. |
| 7,617,163 B2 | 11/2009 | Ben-Hur et al. |
| 7,676,442 B2 | 3/2010 | Ben-Hur et al. |
| 7,778,693 B2 | 8/2010 | Barbour et al. |
| 7,844,324 B2 | 11/2010 | Särkelä et al. |
| 7,949,389 B2 | 5/2011 | Wolfberg et al. |
| 8,046,058 B2 | 10/2011 | Lin et al. |
| 8,118,751 B2 | 2/2012 | Dobak, III |
| 8,221,330 B2 | 7/2012 | Sarkela et al. |
| 8,346,349 B2 | 1/2013 | Guttag et al. |
| 2001/0034488 A1 | 10/2001 | Policker et al. |
| 2002/0103512 A1 | 8/2002 | Echauz et al. |
| 2002/0128563 A1 | 9/2002 | Carlson et al. |
| 2002/0128564 A1 | 9/2002 | Carlson et al. |
| 2003/0199937 A1 | 10/2003 | Carlson et al. |
| 2003/0204146 A1 | 10/2003 | Carlson |
| 2003/0233048 A1 | 12/2003 | Silverman et al. |
| 2004/0039268 A1 | 2/2004 | Barbour et al. |
| 2004/0068199 A1 | 4/2004 | Echauz et al. |
| 2004/0147815 A1 | 7/2004 | Skinner |
| 2004/0176696 A1 | 9/2004 | Mortara |
| 2004/0230105 A1 | 11/2004 | Geva et al. |
| 2005/0010124 A1 | 1/2005 | Couderc et al. |
| 2005/0085734 A1 | 4/2005 | Tehrani |
| 2005/0222515 A1 | 10/2005 | Polyshchuk et al. |
| 2005/0251051 A1 | 11/2005 | Pougatchev et al. |
| 2006/0056655 A1 | 3/2006 | Wen et al. |
| 2006/0074451 A1 | 4/2006 | Chen et al. |
| 2006/0178586 A1 | 8/2006 | Dobak, III |
| 2006/0247546 A1 | 11/2006 | Imose |
| 2007/0032733 A1 | 2/2007 | Burton |
| 2007/0118054 A1 | 5/2007 | Pinhas et al. |
| 2008/0021336 A1 | 1/2008 | Dobak |
| 2008/0039733 A1 | 2/2008 | Unver et al. |
| 2008/0097537 A1 | 4/2008 | Duann et al. |
| 2008/0097940 A1 | 4/2008 | Ben-Hur et al. |
| 2008/0154144 A1 | 6/2008 | Unver et al. |
| 2008/0194981 A1 | 8/2008 | Sarkela et al. |
| 2009/0192394 A1 | 7/2009 | Guttag et al. |
| 2009/0275808 A1 | 11/2009 | DiMaio et al. |
| 2009/0318983 A1 | 12/2009 | Armoundas et al. |
| 2010/0016748 A1 | 1/2010 | Syed et al. |
| 2010/0049063 A1 | 2/2010 | Dobak, III |
| 2010/0179395 A1 | 7/2010 | Bloem |
| 2011/0087127 A1 | 4/2011 | Särkelä et al. |
| 2011/0137189 A1 | 6/2011 | Kuo et al. |
| 2011/0295096 A1 | 12/2011 | Bibian et al. |
| 2012/0004564 A1 | 1/2012 | Dobak, III |
| 2012/0136226 A1 | 5/2012 | Wilke |
| 2012/0172680 A1 | 7/2012 | Gelfand et al. |
| 2013/0046193 A1 | 2/2013 | Guttag et al. |

OTHER PUBLICATIONS

Vullings et al., "Automated ECG segmentation with Dynamic Time Warping," Proceedings of the 20th Annual International Conference of the IEEE Engineering in Medicine and Biology Society, vol. 20, No. 1, 1998, pp. 163-166.

Vyklicky et al., "Analysis of Dynamic Changes in ECG Signals during Optical Mapping by Dynamic Time Warping," Computers in Cardiology, 2005, vol. 32, pp. 543-546.

International Search Report and Written Opinion of the International Searching Authority for International Application No. PCT/US2009/000279, mailed Apr. 15, 2009 (14 pgs.).

Syed et al., "Abstract 2123: ECG Markers to Predict Cardiovascular Death: Heart Rate Variability, Deceleration Capacity and Morphologic Variability in Non-ST-Elevation ACS from the MERLIN-TIMI-36 Trial," American Heart Association, Circulation, 2008;118:S_670, (3 pgs).

Syed et al., "Abstract 2850: Morphological Variability: A New Electrocardiographic Technique for Risk Stratification After NSTEACS," American Heart Association, Circulation, 2007;116:11_634; American Heart Association Scientific Sessions, Orlando, FL, Nov. 6, 2007, (20 pgs).

Anthony Hunt, "T Wave Alternans in high arrhythmic risk patients: Analysis in time and frequency domains: A pilot study," BMC Cardiovascular Disorders, Mar. 12, 2002, pp. 1-7.

Michael J. Lisenby and Philip C. Richardson, "The Beatquency Domain: An Unusual Application of the Fast Fourier Transform," IEEE Transactions on Biomedical Engineering, vol. BME-24, No. 4, Jul. 1977, pp. 405-408.

Laguna et al., "Repolarization Alternans Detection Using the KL Transform and the Beatquency Spectrum," Centro Politécnico Superior, University of Zaragoza Spain, Health Science Technology Division, Harvard-MIT, Cambridge, USA, 1996, pp. 673-676.

Bloomfield et al., "Interpretation and Classification of Microvolt T Wave Alternans Tests," Journal of Cardiovascular Electrophysiology, vol. 13, No. 5, May 2002, pp. 502-512.

Bakhshi, et al., Abstract of "Non-Linear Trend Estimation of Cardiac Repolarization using Wavelet Thresholding for Improved T-wave Alternans Analysis," Digital Signal Processing, Feb. 10, 2013, pp. 1-25.

Paul S. Addison, "Wavelet transforms and the ECG: a review," Topical Review, Institute of Physics Publishing, Physiological Measurement 26 (2005) pp. R155-R199.

Abstract of "A classification scheme for ventricular arrhythmias using wavelets analysis," Medical & Biological Engineering & Computing, Feb. 2013, vol. 51, Issue 1-2, pp. 153-164 (1 page).

* cited by examiner

METHOD AND APPARATUS FOR BEAT-SPACE FREQUENCY DOMAIN PREDICTION OF CARDIOVASCULAR DEATH AFTER ACUTE CORONARY EVENT

CROSS REFERENCE TO PRIOR APPLICATIONS

This application claims the benefit of U.S. Provisional Patent Application No. 61/835,251 filed on Jun. 14, 2013, the entire disclosure of which is incorporated by reference herein.

FIELD OF THE INVENTION

The invention relates to a method and apparatus for generally to medical prognosis and more specifically to the prediction of cardiovascular death following an acute cardiac event.

BACKGROUND OF THE INVENTION

Recently there has been an increased awareness that machine learning can be used in the prediction of adverse medical outcomes. The accuracy of such predictions made by computers using machine learning is predicated on the computer's ability to extract the right information from the data. This extraction is termed feature extraction, feature construction or feature engineering.

The ability to extract the useful features in cardiac events is an important problem because millions of acute coronary events occur each year in the United States alone, resulting in the death of 1 out of 6 deaths in the US. Further, 8-19% of those Americans who had a heart attack will die within 12 months of discharge from the hospital. If physicians could accurately identify high-risk patients, i.e. stratify the risk of death, it may be possible to improve the matching of patients to therapy and thereby potentially improve outcomes. One way this might be accomplished is by the analysis of electrocardiograms (ECG) according to their various characteristics.

An ECG is a substantially repeating pattern that measures the electrical activity of the heart. The ECG is only quasi-periodic due to natural variations in heart rate. This variation in heart rate is a characteristic that may be analyzed and is termed Heart Rate Variability (HRV). One example of HRV is the standard deviation of all "normal" heart beat intervals, termed (HRV-SDNN).

A second characteristic that may be analyzed is the morphological variability (MV) in the ECG signal. MV measures the beat to beat variability in the shape of the beats in a patient's long term ECG signal. MV is determined by obtaining an ECG, and, after preprocessing to clean the signal, segmenting the signal into a time series of beats. For each pair of beats, the differences in beat to beat morphology are measured as morphological distances (MD) using dynamic time warping. (See U.S. Pat. No. 8,346,349, the entire contents of which are herein incorporated by reference in their entirely.) The series of inter-beat distances is termed the MD time series. The MD time series is then divided into fixed time intervals or window segments and the power spectral density of each window then determined. The power spectral density in a 0.30-0.55 Hz frequency band, termed a diagnostic band, in each window is then measured. The 90th percentile of the spectral energies of the diagnostic band in all the windows is the Morphologic Variability (MV) of the ECG. Morphological variability may be used as an indicator that unless treated, the patient is at a higher risk of dying within a predetermined period.

Thus there exist several frequency domain analyses, in which periodic changes are measured. Much work has been performed in frequency domain analyses of ECG signals. However, in the frequency domain, the quasi-periodicity of the ECG introduces significant problem. For example assume that there are two patients with constant heart rates of 60 and 120 beats-per-minute respectively. A frequency domain of 0.5 Hz (sampled every 2 seconds) corresponds to every 2 beats in the first patient but every 4 beats in the second. However in a beat-frequency domain where the notion of frequency is expressed with respect to heartbeats rather than time, every 2 beats corresponds to 0.5 Hz in the first patient but 1.0 Hz in the second. Thus the frequency bands measured in "time-space" and "beat-space" differ. Which frequency domain should be used to analyze the ECG depends on whether the phenomenon of interest is expected to be periodic with respect to time, or periodic with respect to heartbeats. The choice of the "wrong" type of frequency domain may result in ambiguous observations when viewed across patients and when viewed across time for any given patient.

The present invention addresses this issue.

SUMMARY OF THE INVENTION

In one aspect, the invention relates to a method for the machine generation of a model for predicting death within a predetermined period following the occurrence of a cardiac event. In one embodiment the method includes the steps of: obtaining an ECG of interest, the ECG having a plurality of ECG characteristics; obtaining a time series of one of the ECG characteristics of the plurality of ECG characteristics; dividing the time series into a plurality of window segments; converting the time series from time-space to beat-space; computing the power in various frequency bands of each window segment; computing the 90th percentile of the spectral energies across all window segments for each frequency band; and inputting the data into a machine learning program to generate a weighted risk vector. In another embodiment the method further includes the step of removing noise from the time series. In yet another embodiment the machine learning program is a L1-regularized logistic regression machine learning program.

In another aspect the invention relates to a method for the machine generation of a model for predicting patient outcome following the occurrence of a medical event. In one embodiment the method includes the steps of obtaining a physiological signal of interest, the physiological signal having a characteristic; obtaining a time series of a signal characteristic; dividing the time series into a plurality of window segments; converting the time series from time-space to inverse physiological event space; computing the power in various frequency bands of each window segment; computing the 90th percentile of the spectral energies of various frequency bands in all window segments; and inputting the data into a machine learning program to generate a weighted risk vector. In another embodiment the machine learning program is a L1-regularized logistic regression machine learning program.

In another aspect the invention relates to a method of predicting death, within a predetermined period, of a patient following the occurrence of a cardiac event. In one embodiment, the method includes the steps of obtaining an ECG of the patient of interest, the ECG having a plurality of ECG characteristics; obtaining a time series of one of the ECG characteristics of the plurality of ECG characteristics; dividing the time series into a plurality of window segments; converting the time series from time-space to beat-space; computing the power in various frequency bands of each window segment; computing the 90th percentile of the spectral energies across all window segments for each frequency band; and computing the risk by multiplying the 90th percentile spectral energies by a weighted risk vector.

DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

FIG. 4 (a, b) are diagrams of the same morphological distance (MD) time series as graphed in time-space (FIG. 4(a)) and beat-space (FIG. 4(b))

DESCRIPTION OF A PREFERRED EMBODIMENT

Figure 1:
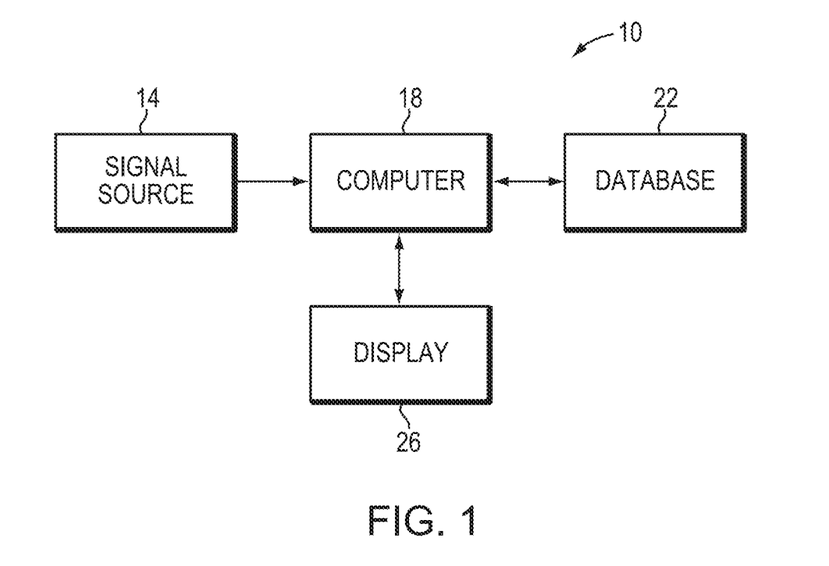
FIG. 1 is a block diagram of an embodiment of a system constructed in accordance with the invention.

Referring to FIG. 1, a system 10 constructed in accordance with the invention includes a device 14 connected to receive a periodic or quasi-periodic physiologic signal, a computer or processor 18 in communication with device 14, a database 22 in communication with the computer or processor 18 and a display 26 connected to communicate with the processor 18. Although the system, in the embodiment shown, is depicted with the processor 18 as being connected directly to the physiological signal device 14, the data from device 14 could be input to the database 22 and the data analyzed subsequently by the processor 18. Although the embodiment shown depicts the components as individual devices, it is possible to have the processor included with the signal source, such as an ECG, a database and a display unit in a single device.

The method and system herein described may be considered as two parts. The purpose first part is to find the correct metric for prognosis of a patient, and the second is to use that metric to make a prognosis for a specific patient. Each part will be described individually. In the first part the process for determining the prognosis of a patient is described. In the embodiment first described, the metric sought is useful in predicting patient outcome after a cardiac event using an ECG as a signal source.

In one embodiment, the physiological quasi-periodic signal used for prognosis is generated by a patient's heartbeat and ECG is the device 14, recording the signal. Further, although the ECG is used in this discussion as the physiological signal, other periodic or quasi-periodic physiological signals, such as respiration, may be used with the technique to predict the course of a patient's health.

Figure 2:
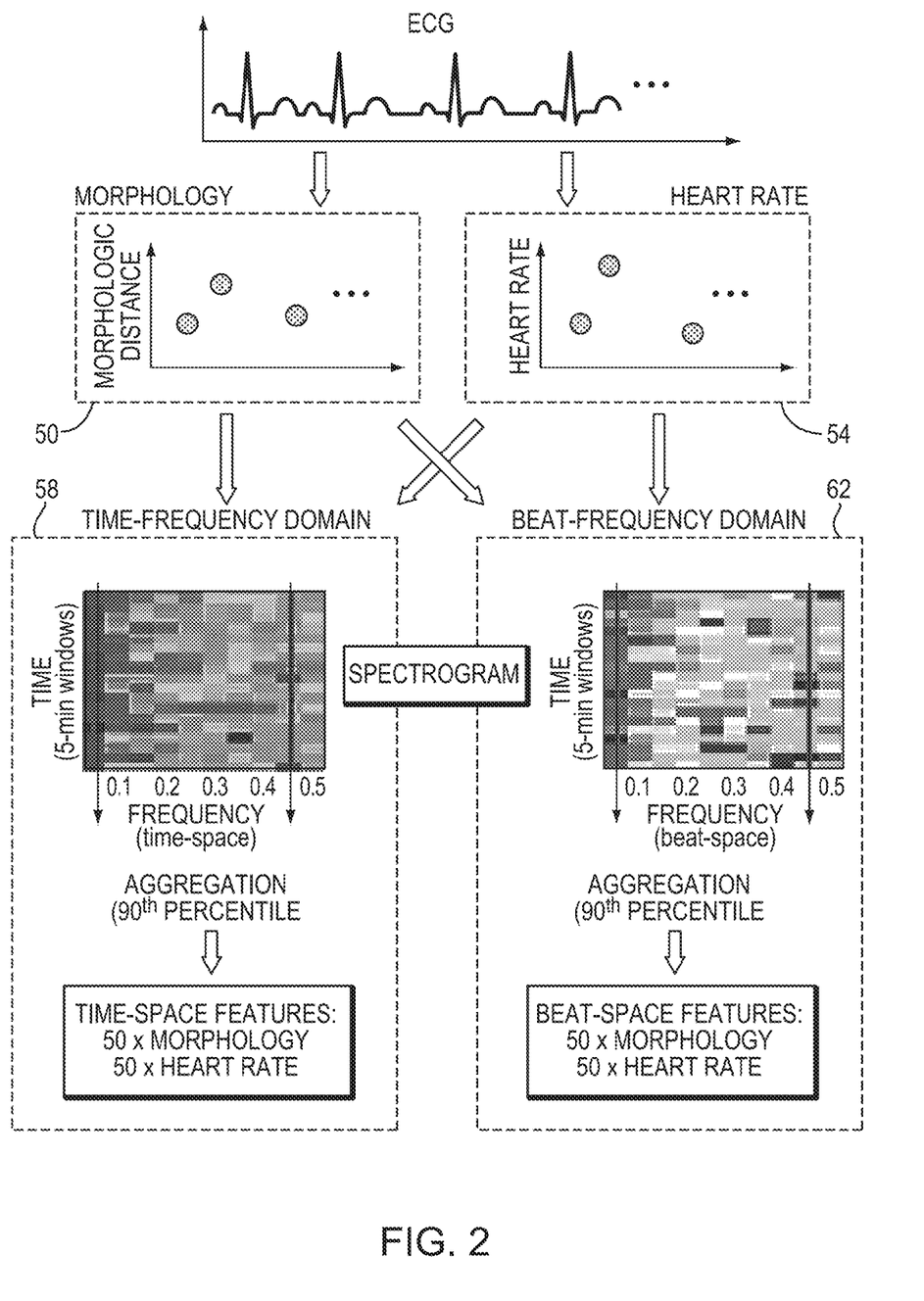
FIG. 2 is a block diagram of an embodiment of the process of the invention.

Referring to FIG. 2, in brief overview, this discussion of an embodiment of the invention considers both the morphological distance 50 and the heart rate 54 of a patient with the intent of generating a prognosis for the patient. The heart rate and morphological distance is determined in both the time-frequency 58 and the beat frequency domains 62. The power spectrum for a defined band in each of the defined time windows is measured. The 90th percentile of the spectral energies of the diagnostic band in all the windows is then used to quantify the patient's condition. Although in this embodiment both the heart rate and morphological distance are used, it is not required that they be both used.

As stated above the discussion of the system and process is directed toward the use of an ECG to determine patient outcome, but other periodic signals may be used to determine other components of the patient's status. Because an ECG is periodic with respect to heartbeats but not necessarily periodic with respect to time, feature extraction performed in the frequency domain may be improved if quantification occurs with respect to heartbeats rather than with respect to time. Some prior work used relatively simple beat-frequency domain analysis (termed beatquency and interval spectrum) but a comprehensive analysis of the entire beat-frequency spectrum is lacking.

To address this lack of analysis, the present method and system applies machine learning to long-term ECG signals to predict adverse cardiovascular events, such as death, after a specific cardiac event. In one embodiment the cardiac event was non-ST-elevation acute coronary syndrome (which includes non-ST-elevation). For this embodiment, the features used for analysis included frequency-domain features based both on ECG morphology and features based on heart rate, as adjusted for the TIMI Risk Score (TRS), B-type natriuretic peptide (BNP), and left ventricular ejection fraction (LVEF). TRS summarizes the effects of numerous risk factors including age, elevated biomarkers, and presence of coronary artery disease. BNP is a blood biomarker that is elevated when the myocardium is stretched, and LVEF indicates the ability of the heart to eject blood.

Two separate datasets were used to develop this method of patient prognosis based on ECG characteristics. One data set was used for training and validation of the machine learning model. A smaller dataset was used as a separate, holdout dataset to assess performance of the model.

The training dataset used in training the computer model consisted of 2302 patients in the placebo portion of a clinical trial performed to discover the effectiveness of a drug, for cardiac issues. Only the placebo portion of the trial was used because patients in the treatment portion were prescribed a drug that may have anti-arrhythmic properties and thus might affect their ECG measures. In this trial 50 cardiovascular deaths occurred within 90 days of the initial cardiac event. The median follow-up period for the survivors was 1 year. For each patient used in the training set, the first 24 hours of Holter ECG data collected at the standard 128 Hz was used for feature extraction. The features extracted include both ECG morphology based features and heart rate based features. As discussed above, the morphology based and the heart rate features were computed in the frequency domain in both time-space and beat-space. In this example the system was programmed to determine the probability of death with 90 days of a cardiac event, but any time period may be used and any other outcome predicted.

The holdout dataset used for the measurement of the performance of the model consisted of 765 patients. These patients were from a separate clinical trial. In this trial, 14 cardiovascular deaths occurred within 90 days of the initial cardiac event.

Figure 3:
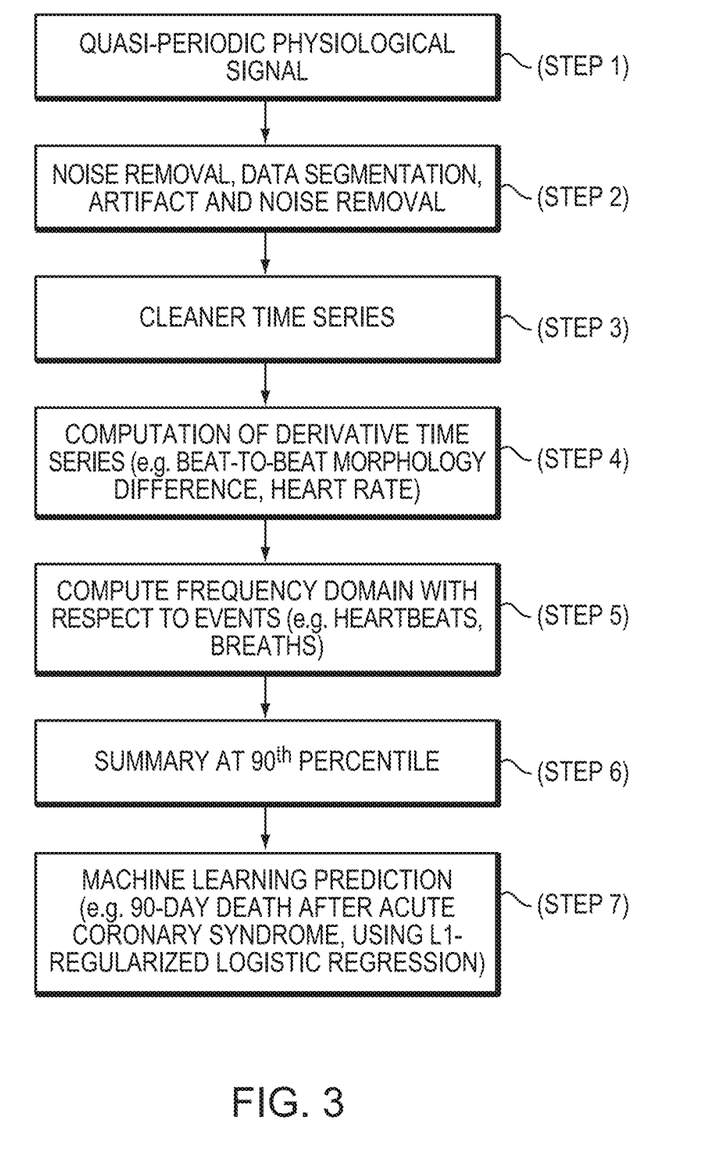
FIG. 3 is a block diagram of an embodiment of an algorithm for determining the metric for the prediction of an adverse outcome, such as death, after a coronary event using information from a number of patients and, constructed according to the present invention.

Referring also to FIG. 3, the ECG morphological features extracted from the ECG morphology were based on the Morphologic Variability metric, and the ECG heart rate features were extracted in a similar fashion, based on a second ECG characteristic, the heart rate. Morphologic Variability as discussed above, quantifies the variability in beat-to-beat ECG morphology over a period of time. In one embodiment the period was a day. First, the quasi-periodic signal is collected (Step 1); the data cleaned to remove noise and artifacts; and the data segmented (Step 2), resulting in a cleaner time series (Step 3). The input ECG signal is next converted into a time series based on different characteristics; e.g. beat-to-beat difference time series (the MD time series) and the heart rate series (Step 4). Each resulting time series is then divided into 5-minute window segments (not shown).

Next the time series in each window is converted from time-space to beat-space, and is then converted into the frequency domain (Step 5). It should be noted that although in this embodiment the space is refereed to as beat space (inverse heart beats as a metric) the space metric is determined by what the periodic signal is. For example if respiration is used, the space would be breath-space with inverse breaths as a metric.

This beat-space conversion enables each individual window segment to be converted to the appropriate beat-space frequency domain. The power in various frequency bands of each window segment is then computed as is done in the prior art MV computations.

The power spectrum is then determined for each window segment and for each frequency band, the 90th percentile of the spectral energies over all the windows is then determined (Step 6). This data is a portion of the input data into the L1-regularized logistic regression machine learning program (Step 7).

Figure 4:
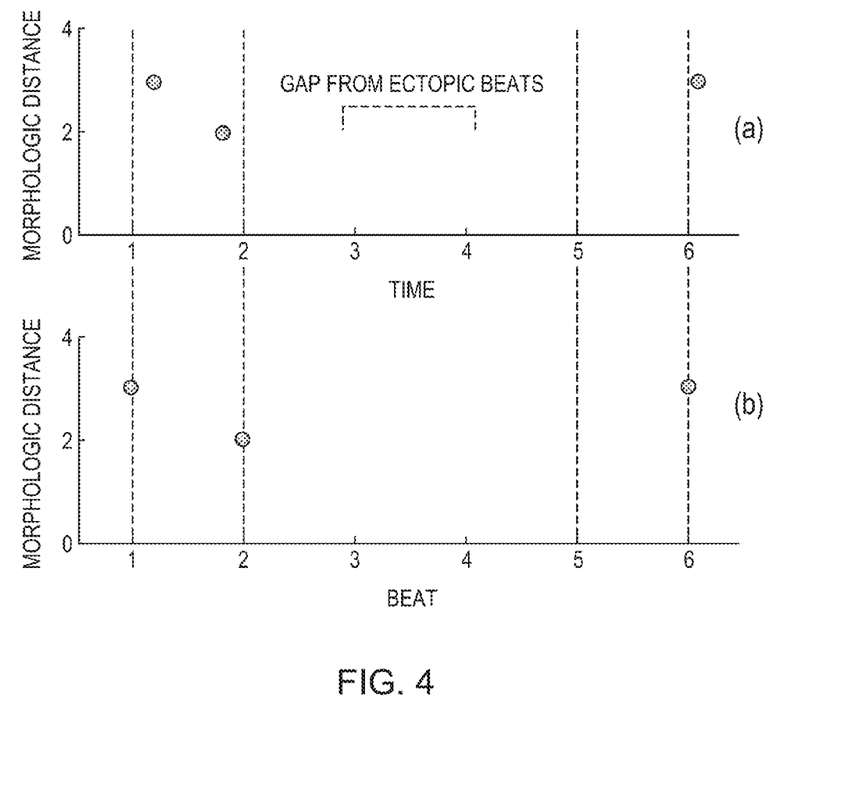

Referring to FIGS. 4(a, b), to perform the conversion of the time-series to the beat-series, the MD time series are aligned to single beat intervals. If beats, such as ectopic beats, have been removed by the preprocessing step, the gap in the number of beats is estimated by averaging the time intervals of the beats immediately before and immediately after the gap. At this point the frequency domain is measured in inverse beats (cycles per beat) rather than inverse time (Hz.).

In one embodiment, the frequency spectrum in inverse beats is next divided into 50 frequency bands, ranging from 0.01 to 0.50 inverse beats. For each frequency band, the 90th percentile of the energies over all 5-minute windows is taken to be the value for the feature corresponding to that frequency. This results in a feature vector of length 50 for each patient.

For the morphological analysis, the Weighted Morphologic Variability is then calculated as the weighted sum of the energies in all the frequency bands. That is:

$$WMV = \vec{w}^T \vec{x}$$

where $w^T$ is the transpose of the weights found by the learning algorithm described below and x is the input feature vector. Note that the w also is a vector of the same length as the input feature vector, while WMV is a single number.

For the Heart Rate Variability analysis, a Weighted Heart Rate Variability can be calculated by replacing the x input feature vector with the corresponding feature vector derived from the heart rate time series. In one embodiment of the feature extraction, the input ECG signal is converted into a time series of instantaneous heart rates using the time interval between each heartbeat. This time series is then divided into 5-minute window segments and the individual window segments converted from time-space to beat-space and then converted into the frequency domain. As with the Morphological Variability metric, the power in each of the frequency bands are aggregated at the 90th percentile as a measure of the value of the feature corresponding to that band. In one embodiment, 50 feature vectors from 0.01 to 0.50 inverse beats (cycles/beat) are extracted.

In one embodiment, the Machine Learning Protocol began by dividing the data into training and test sets in a 2:1 ratio. Ratios such as 3:2, 1:1, and 4:1 are used in other embodiments. This random division procedure was performed to ensure equal representation of both classes, those that experienced an event and those who did not.

In one embodiment, a regression analysis was used to separate patient classes but other machine learning algorithms can be used. In one embodiment, to train the computer, a L1-regularized logistic regression model as implemented in Liblinear (Machine Learning Group, National Taiwan University, Taipei, Taiwan) was trained on the training set and validated on the test set. L1 regularization was chosen to perform implicit feature selection because it was expected that only a relatively small subset of the frequency domain would contain pertinent prognostic information. During training, cross validation was used to optimize the cost parameter.

Because only 2.2% of the patients experienced a fatal event, another parameter, the asymmetric cost parameter, was set to the class imbalance. The frequency-domain features were standardized by subtracting the mean and dividing by the standard deviation.

The area under the receiver operating characteristic curve (AUC) was used to assess the performance of the machine learning model. To reduce the effects of selecting an overly optimistic or pessimistic test set, the training/test split was repeated 1000 times and the results are reported only on the 1000 test splits. The end result of the model is a weighted risk vector that is that contains the weighted values for determining whether the patient will have an adverse event within a predetermined number of days. In the example shown the weighted risk vector is used to determine whether a patient will die within 90 days of a cardiac event.

Once this procedure was used, the difference between time-space and beat-space frequency band was assessed. The energy in defined frequency bands (low frequency (0.04 to 0.15 Hz.) and high frequency bands (0.15 to 0.40 Hz) from heart rate variability and diagnostic frequency (0.03 to 0.55 Hz) from morphologic variability) was determined for each 5-minute window for each patient.

To determine the frequency bands in beat-space corresponding to those in time-space, the energy in all possible beat-space frequency bands ranging from 0.01 to 0.50 inverse beats was calculated. The frequency band with the highest correlation coefficient was defined as the corresponding frequency band in beat-space. The amount of variance in the time-space values was computed by taking the square of the correlation coefficient. To weigh the data from each patient equally, 10 randomly selected 5-minute windows from each patient were chosen, resulting in comparisons of approximately 23,000 5-minute windows.

Two different types of features: morphology and heart rate (each a 50 dimensional feature vector) were used to compare the results in beat-space and time-space.

The area under the receiver operating characteristic curve (AUC) was then determined. This area can be interpreted as the probability that when a metric for a patient who dies within a predetermined period is compared to another who does not die during that period, the metric ranks the patient who died as having a higher risk. Statistical significance of the difference in AUC was assessed by a two-tailed paired t-test over 1000 random training/test splits of the data, and in the holdout set using the same 1000 models trained from the 1000 training splits.

A hazard ratio (HR) using the Cox proportional hazards regression model was also calculated. The HR takes into consideration censoring and quantifies the rate of events in the high risk group against the low risk group. To aid in interpreting the models, the HR of the continuous logistic regression values of the upper quartile of each test set was compared to the patients in the remaining three quartiles. For example, if the cutoff for the upper quartile was 3.0, the patients with a value of ≥3.0 were compared to patients with a value <3.0. A HR higher than 1 indicates that patients predicted to be at high risk died more frequently compared to patients predicted to be at lower risk.

The HR was also adjusted for the clinical measures TRS, BNP and LVEF. The TRS is defined as the number of risk factors (out of 7) that a person has, and thus ranges from 0 to 7. Patients were divided into low (TRS≤2), moderate (3≤TRS≤5), and high-risk (TRS≥5) groups Two binary values were assigned to indicate moderate and high-risk groups respectively. These two values were used as another measure to assess the value of the machine learning model. Similarly, adjusting for BNP and LVEF are done by established cutoffs: >80 pg/ml and ≤40%. For example, if a patient has TRS=4, BNP=100, and LVEF=30, then the TRS (moderate-risk)=1, TRS (high-risk)=0; BPN (high-risk)=1 and LVEF (high-risk)=1. These four parameters are used in HR computation to derive "adjusted" HR's that quantify the additional information provided by the machine learning model.

The differences between the beat-space and time-space results are next discussed for the ECG measurements.

The frequency domains in beat-space and time-space are verifiably different. As shown in Table 1, the correlation coefficients between beat-space and time-space frequency bands ranged from 0.65 to 0.84, corresponding to from 40% to 70% of the explained variance (based on the squared correlation, or R-squared values), depending upon the frequency band in time-space and whether morphology (diagnostic frequency of Morphologic Variability) or heart rate (Low Frequency and High Frequency of Heart Rate Variability) is analyzed.

Morphology Based Metrics

The performance of the morphology based metrics may also vary significantly depending on whether they are measured in time-space or beat-space. The relative performance of machine learning models using 50 frequency domain features based only on ECG morphology in beat-space was compared to ECG morphology in time-space (Table 2). A slight increase in AUC was observed (0.701 vs 0.697, p<0.05) in the training set. In the holdout set, the AUC was significantly higher for beat-space morphology-based features (0.729 vs 0.710, p<0.001) (Table 2). In the validation splits of the training set, the beat-space model HR was 3.8, 3.4 after adjusting for TRS, and 3.1 after adjusting for TRS, BNP and LVEF (Table 3).

Heart Rate Based Metrics

The relative performance of machine learning models using 50 frequency domain features based only on heart rate in beat-space compared to time-space are also shown in Table 2. A larger increase in AUC (0.759 vs 0.726, p<0.001) was observed in this case in the training set and the holdout set (0.725 vs 0.651, p<0.001). In the validation splits of the training set, the beat-space model HR was 5.1, and 4.1 after adjusting for TRS, and 3.5 after adjusting for TRS, BNP and LVEF (Table 3).

Both Morphology and Heart Rate Based Features

The relative performance of machine learning models using both morphology and heart rate based features (100 features total, Table 2). The AUC was similar in the training set (0.755 vs 0.755) but significantly higher in the holdout set for beat-space features (0.741 vs 0.713, p<0.001). In the validation splits of the training set, the HR was 4.8, and 3.9 after adjusting for TRS, and 2.9 after adjusting for TRS, BNP and LVEF (Table 3).

The data demonstrates that computing frequency-domain features from an ECG in beat-space outperforms time-space when used to predict the probability of death after an acute coronary event. These results hold true for morphology-based features, heart rate-based features, individually and when both are combined. Furthermore, the models remain accurate after adjusting for TRS.

Figure 5:
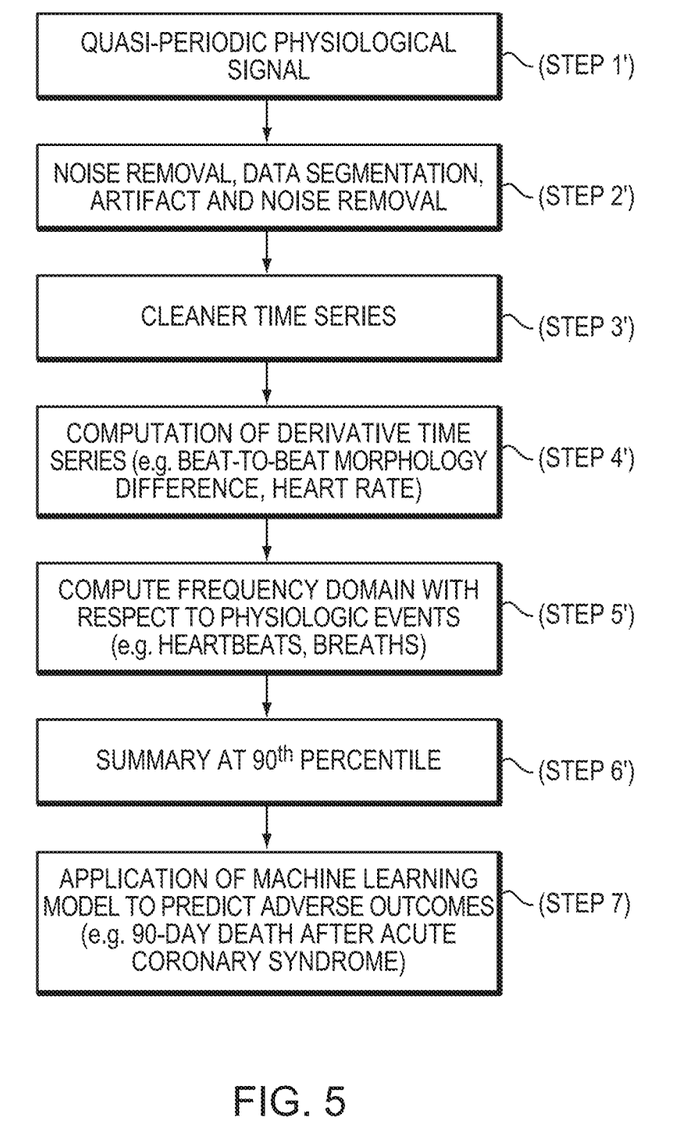
FIG. 5 is a block diagram of an embodiment of an algorithm the prediction of death after a coronary event for a given patient.

Once the model generates a weighted risk vector, the weighted risk vector is then used to predict an outcome for a given patient. Referring to FIG. 5 the first 6 steps (Steps l'-6') of the algorithm to predict an outcome for a specific patient is the same as the steps that are used to generate the model. However once the feature vector is generated for the patient (Step 6') that patient feature vector is multiplied by the weighted risk vector generated by the model (Step 7) to generate a number, the risk index. That risk index is then compared with a predetermined limit and any value above that safe limit indicates a significant probability that the patient will have an adverse event (for example death) within a predetermined time period, in this example 90 days. In one embodiment the limit is some quartile. That is, one could define the risk of death is elevated if the patient falls within the top 25% of patients having a prior cardiac event. Table 4 shows the prediction performance of the system based on Heart Rate Variability over various time frames and various outcomes.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes, and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

TABLE 1

Correlation coefficients between the frequency bands in beat-space and time-space.

| ECG Metric Frequency Band | Frequency-band (time-space) | Pearson's r | Spearman's rho | Kendall's tau |
|---|---|---|---|---|
| HRV-LF (Low Frequency) | 0.04-0.15 Hz | 0.6470 | 0.7208 | 0.5341 |
| HRV-HF (High Frequency) | 0.15-0.40 Hz | 0.8390 | 0.9326 | 0.7750 |
| MV-DF (Diagnostic Frequency) | 0.30-0.55 Hz | 0.7358 | 0.7073 | 0.5279 |

TABLE 2

Table 2. Prediction performance using frequency-domain features in beat-space and time-space, reported using AUC, and the standard error is reported in parenthesis. Bold indicates the higher c-index in each row (beat-space vs time-space).

|  | Features used (# of features) | Beat-space | Time-space | p (beat-space VS time-space) |
|---|---|---|---|---|
| Training Set (1000 repeats of 2:1 split) | Morphology (50) | 0.7008 (0.0018) | 0.6988 (0.0019) | 0.033 |
|  | Rate (50) | 0.7590 (0.0015) | 0.7259 (0.0018) | <0.001 |
|  | Morphology + Rate (100) | 0.7551 (0.0015) | 0.7545 (0.0018) | 0.720 |
| Holdout Set (1000 models from training set) | Morphology (50) | 0.7285 (0.0010) | 0.7104 (0.0013) | <0.001 |
|  | Rate (50) | 0.7249 (0.0006) | 0.6509 (0.0010) | <0.001 |
|  | Morphology + Rate (100) | 0.7412 (0.0006) | 0.7131 (0.0011) | <0.001 |

TABLE 3

Table 3: Prediction performance using frequency-domain features in beat-space and time-space, reported using the hazard ratio, and the standard error is shown in parenthesis.

| Features used (# of features) | 90-day Harzard Ratio (HR) | 90-day HR (adjusted for TRS) | 90-day HR (adjusted for TRS, BNP, LVEF)* |
|---|---|---|---|
| Beat-space Morphology (50) | 3.78 | 3.36 | 3.07 |
| Beat-space Rate (50) | 5.08 | 4.08 | 3.46 |
| Beat-space Morphology + Rate (100) | 4.83 | 3.94 | 2.92 |

TABLE 4

Table 4: Prediction performance using 50 frequency-domain features based on heart rate variability in beat-space and time-space, reported using AUC. The standard error is reported in parenthesis. Bold indicates the higher c-index in each row (beat-space vs time-space). All differences are significant.

|  | Adverse Outcome (Time-frame) | Time-frame | Beat-space | Time-space |
|---|---|---|---|---|
| Training Set (1000 repeats of 2:1 split) | Cardiovascular death | 90-days | 0.7590 (0.0015) | 0.7259 (0.0018) |
| Training Set (1000 repeats of 2:1 split) | Cardiovascular death | 1-year | 0.7505 (0.0012) | 0.7024 (0.0012) |
| Training Set (1000 repeats of 2:1 split) | Cardiovascular death in Low TRS Patients | 1-year | 0.7630 (0.0017) | 0.7075 (0.0020) |
| Training Set (100 repeats of 2:1 split) | Sudden Cardiac Death | 1-year | 0.7121 (0.0049) | 0.6607 (0.0056) |

What is claimed is:

1. A method for the machine generation of a model for predicting death within a predetermined period following the occurrence of a cardiac event, the method comprising the steps of:
   obtaining an ECG of interest from a plurality of patients having a plurality of outcomes, the ECG having a plurality of ECG characteristics;
   obtaining a time series of one of the ECG characteristics of the plurality of ECG characteristics;
   dividing the time series into a plurality of window segments;
   converting the time series from time-space to beat-space;
   computing the power in various frequency bands of each window segment;
   computing the 90th percentile of the spectral energies across all window segments for each frequency band to generate spectral energy data; and
   inputting the spectral energy data into a machine learning program to obtain a weighted risk vector.

2. The method of claim 1 further comprising the step of removing noise from the time series.

3. The method of claim 1 wherein the machine learning program is an L1 regularized logistic regression machine learning program.

4. A method for the machine generation of a model for predicting patient outcome following the occurrence of a medical event, the method comprising the steps of:
   obtaining a physiological signal of interest from a plurality of patients having a plurality of outcomes, the physiological signal having a characteristic;
   obtaining a time series of a signal characteristic;
   dividing the time series into a plurality of window segments;
   converting the time series from time-space to an inverse physiological event space;
   computing the power spectrum for a characteristic frequency band for each window segment;

computing the 90th percentile of the spectral energies across all window segments for each frequency band to generate spectral energy data; and inputting the spectral energy data into the L1-regularized logistic regression machine learning program to generate a weighted risk vector.

5. A method of predicting death within a predetermined period, of a patient following the occurrence of a cardiac event, the method comprising the steps of:

obtaining, using an ECG module, an ECG of the patient of interest, the ECG having a plurality of ECG characteristics;

obtaining, using a processor in communication with the ECG module, a time series of one of the ECG characteristics of the plurality of ECG characteristics;

dividing, using the processor, the time series into a plurality of window segments;

converting, using the processor, the time series from time-space to beat-space;

computing, using the processor, the power in various frequency bands of each window segment;

computing, using the processor, the 90th percentile of the spectral energies across all window segments for each frequency band;

computing, using the processor, a risk by multiplying the 90th percentile spectral energies by a weighted risk vector and comparing the result to a predetermined value, and displaying, on a display, a prediction of the death of the patient in response to the comparison.

* * * * *